(12) United States Patent
Borek et al.

(10) Patent No.: US 8,007,777 B2
(45) Date of Patent: Aug. 30, 2011

(54) DELIVERY SYSTEM FOR BIOLOGICAL COMPONENT

(75) Inventors: Tanya Borek, North Bend, WA (US); Terri Butler, Kirkland, WA (US); Catherine Federici, Seattle, WA (US); Michael P. Hite, Seattle, WA (US); Christopher London, Bellevue, WA (US); Stephen J. Turner, Covington, WA (US)

(73) Assignee: Nutraceutix, Inc., Redmond, WA (US)

( * ) Notice: Subject to any disclaimer, the term of this patent is extended or adjusted under 35 U.S.C. 154(b) by 0 days.

(21) Appl. No.: 10/261,639

(22) Filed: Sep. 30, 2002

(65) Prior Publication Data

US 2003/0096002 A1    May 22, 2003

Related U.S. Application Data

(60) Provisional application No. 60/325,937, filed on Sep. 28, 2001.

(51) Int. Cl.
*A01N 63/00* (2006.01)
(52) U.S. Cl. .......... 424/93.1; 424/93.45; 424/93.4; 424/464; 424/93.46; 424/93.5; 424/93.51; 435/252.1; 435/252.9
(58) Field of Classification Search .......... 424/93.1, 424/93.4, 93.41, 93.42, 93.43, 93.44, 93.45, 424/93.46, 94.1; 435/252.1, 252.9
See application file for complete search history.

(56) References Cited

U.S. PATENT DOCUMENTS

| | | | |
|---|---|---|---|
| 3,072,528 A | 1/1963 | Kludas | |
| 4,264,573 A | 4/1981 | Powell | |
| 4,542,020 A | 9/1985 | Jackson | |
| 4,755,180 A | 7/1988 | Ayer | |
| 4,777,033 A | 10/1988 | Ikura | |
| 4,806,368 A * | 2/1989 | Reddy | 426/61 |
| 4,966,768 A | 10/1990 | Michelucci | |
| 5,194,172 A | 3/1993 | Taneri | |
| 5,213,808 A | 5/1993 | Bar-Shalom et al. | |
| 5,288,507 A * | 2/1994 | Sims et al. | 424/682 |
| 5,419,917 A | 5/1995 | Chen | |
| 5,531,681 A * | 7/1996 | Walton et al. | 604/83 |
| 5,789,446 A * | 8/1998 | Uchiyama et al. | 514/568 |
| 5,830,884 A | 11/1998 | Kasica et al. | |
| 6,090,411 A | 7/2000 | Pillay et al. | |
| 6,127,561 A | 10/2000 | Jeromin | |
| 6,241,983 B1 * | 6/2001 | Paul et al. | 424/93.4 |
| 6,337,091 B1 | 1/2002 | Kim et al. | |
| 6,365,148 B1 * | 4/2002 | Kim et al. | 424/93.1 |
| 6,375,994 B1 | 4/2002 | Paul | |
| 6,403,120 B1 | 6/2002 | Sherman et al. | |
| 6,413,494 B1 * | 7/2002 | Lee et al. | 424/9.1 |
| 6,458,384 B2 * | 10/2002 | Jaenicke et al. | 424/468 |
| 6,479,051 B1 * | 11/2002 | Bruce et al. | 424/93.45 |
| 6,517,868 B2 | 2/2003 | Fassihi et al. | |
| 6,777,000 B2 * | 8/2004 | Ni et al. | 424/488 |
| 6,936,275 B2 | 8/2005 | Fassihi | |
| 7,122,370 B2 | 10/2006 | Porubcan | |
| 7,201,923 B1 | 4/2007 | van Lengerich | |
| 7,229,642 B2 | 6/2007 | Fassihi | |
| 7,498,310 B1 | 3/2009 | Schonrock et al. | |
| 2001/0005513 A1 | 6/2001 | Haan et al. | |
| 2002/0010127 A1 | 1/2002 | Oshlack | |
| 2002/0107495 A1 | 8/2002 | Chen et al. | |
| 2003/0021841 A1 | 1/2003 | Matharu et al. | |

FOREIGN PATENT DOCUMENTS

| | | |
|---|---|---|
| JP | 09110705 | 4/1997 |
| WO | 9748386 | 12/1997 |
| WO | WO 9952507 A1 * | 10/1999 |
| WO | 02094424 | 11/2002 |

OTHER PUBLICATIONS

Pillay et al. J. Controlled Release (2000) 67:67-78.*
Chen et al., Chemical Physical, and Baking Properties of Apple Fiber Compared with Wheat and Oat Bran, Cereal Chemistry, 1988, vol. 65, No. 3, pp. 244-247.
Maggi et al., "Technological and biological evaluation of tablets containing different strains of lactobacilli for vaginal administration," Eu. J. Pharm Biopharm., 2000, vol. 50, No. 3, p. 389-395.
Raffalt, J.D. et al., Proceedings for the international symposium on controlled release bioactive materials, 1999, No. 26, p. 865-6.
curehunter.com/public/keywordSummaryCO09683-witepsol.do, downloaded May 7, 2010.
Webster's II New Riverside University Dictionary (1997) (Houghton-Mifflin: Boston, MA) p. 1175.
www.treetopingredients.com/ applefiber.asp (1 of 3)11/10/210.
Schilling et al. European J Pharma. Biopharma. (2010) 74:352-361.

* cited by examiner

*Primary Examiner* — Susan Hanley
(74) *Attorney, Agent, or Firm* — Miller Nash LLP

(57) ABSTRACT

The invention relates to a controlled release formulation for a probiotic. The formulation contains a hydrophilic agent, an electrolytic agent and a polysaccharide and is in the form of a monolithic tablet for oral delivery to the intestinal system. The probiotic can be lactic acid bacteria.

8 Claims, 13 Drawing Sheets

DELIVERY SYSTEM FOR BIOLOGICAL COMPONENT

CROSS-REFERENCE(S) TO RELATED APPLICATION(S)

This application claims the benefit of U.S. Provisional Application No. 60/325,937 entitled "Delivery System for Biological Component" filed Sep. 28, 2001 hereby incorporated by reference.

BACKGROUND

The present invention is directed to a controlled release solid dosage form for biological components. In addition, the invention is directed to a method of delivery of beneficial microorganisms over an extended timeframe.

As a substance passes through the human gastrointestinal (GI) tract it is subjected to a wide range of pH values ranging from the neutral pH of the mouth, to the acidic conditions of the stomach, to the 5.0-7.5 pH range of the intestinal tract. Because the majority of biologically active components are highly pH sensitive, these changes in pH can cause significant effects upon the stability of the biological component and their ability to function in vivo. For example, many proteins denature in acidic environments; once denatured, their biological activity, if present, significantly differs from the non-denatured state. For a biological component (BC) to be functional, it must survive the gastrointestinal tract with minimal exposure to pH fluctuations. Further, BCs are also sensitive to enzymatic degradation. For example, one barrier to the oral administration of insulin is its susceptibility to enzymatic degradation.

The oral administration of biological components without a controlled release system has as a significant disadvantage not allowing for the biologic to by-pass the low pH and enzyme-rich environment of the stomach, thereby potentially decreasing the viability of the BC. For those devices which employ an enteric coating mechanism to survive the gastric environment, the shortcomings may be two-fold. First, the process of coating the dosage form or its contents may result in significantly lowered viability of the BC. Second, the downfall of merely by-passing the stomach is the explosive delivery of the biologic immediately upon exiting the stomach. This non-specific delivery is ineffectual and primitive in view of certain delivery needs of biological components because the bioavailability of BCs is often site dependent. Biological components may be targeted either through modification of the biologic itself or through the controlled release of the biologic within a desired physiologic window. One such biological component that displays such site-specificity is the lactic acid bacteria, *Lactobacillus Acidophilus* (a probiotic). *L. Acidophilus* is one example of other probiotics, including *Lactobacillus bulgaricus, Lactobacillus casei* subsp. *Rhamnosus, Lactobacillus casei* subsp. *Casei, Lactobacillus salivarius, Lactobacillus brevis, Lactobacillus reuteri, Lactococcus lactis* subsp. *Lactis, Enterococcus faecium, Lactobacillus plantarum, Streptococcus thermophilus, Bifidobacterium infantis, Bifidobacterium Bifidum, Bifidobacterium longum, Saccharomyces boulardii*, and various modified soil organisms.

Each strain of *L. Acidophilus* will attach at a different location of the intestinal tract, preferentially attaching within a region either slightly proximal or distal to other *L. Acidophilus* strains. These preferential regions of attachment are of particular importance relative to employing the bacteria as delivery systems for genomic or proteomic therapy, whether directly or as carriers for other vectors containing genetic or proteomic biologicals.

Beneficial microorganisms, for example, but not limited to, gastrointestinal flora such as lactic acid bacteria and yeast are an essential constituent of metabolism and immune response. Supplementation of beneficial microorganisms is a valid mechanism for replacement of flora lost due to antibiotic treatment, enhancement of naturally-occurring levels of beneficial flora, enhancing competitive inhibition and otherwise preventing enteropathogens, and altering the metabolism of ingested substances. Probiotics are one example of beneficial microorganisms.

Solid oral dosage forms employing controlled release have been increasingly demonstrated to be beneficial to the administration of pharmaceutical compounds, enhancing safety and consumer compliance, minimizing side effects and providing new therapeutic benefits. The four generalized platforms for controlled release solid oral dosage forms are diffusion, reservoir, pore-forming wax, or coated-bead systems. Few have been applied to BCs due to high development costs, bioavailability issues, and stability of the dosage BC within the dosage form. In the past, enteric coating technologies and other mechanisms of delayed release have been limited to features with explosive delivery after the stomach.

Controlled release delivery systems can take many forms including polymeric matrix systems, wax matrix systems, multi-particulate systems, and combinations thereof. The most commonly used delivery systems can be broadly classified as diffusion, reservoir, pore-forming wax, or coated-bead systems. Diffusion devices are composed of a drug dispensed in a polymer which diffuses from the entire physical tablet. Reservoir devices usually consists of a semi-permeable barrier which is involved in the release of the active from a core site within the tablet. Coated-bead systems employ an enteric or pH-sensitive coating of aggregated particles of the active ingredient packaged in capsule form. Pore-forming wax systems incorporate the active ingredient into a wax base and rely upon the rate of diffusion to control the release of the active ingredient.

In tableted, pore forming wax matrices, the BC and a water-soluble polymer are introduced into a wax or wax-like compound such as paraffin or guar gum, and then placed in an aqueous environment so as to allow the water-soluble polymer to dissolve out of the wax, resulting in the formation of pores. Upon contact with the gastrointestinal fluid, the pores facilitate diffusion-mediated release of the BC. The rate of release of the BC is dependent upon non-linear erosion.

Coated-bead systems are one of the few delivery systems available in both tablet and capsule form. The BC encased within a bead using one of the variety of processes available, such as spheronization-extrusion or coating of non-pareils. The coated-BC is then further coated with an enteric coating or employed in a blend of coated-beads with differing release rates for extended release formulations. The BC may also be blended or granulated with polymers before coating to provide an additional level of control. The coated-beads themselves may also be combined with polymers to create a hybrid diffusion or wax-based system. Coated-bead systems are complex to manufacture, requiring large numbers of excipients, use of solvents, and long manufacturing time. The use of such solvents and the manufacturing processes required to apply such solvents may expose the BC to adverse environmental conditions and cause a loss of the viability of the BC. This is especially concerning in the case of lyophilized BCs, where any exposure to moisture may cause significant decreases in viability.

An example of a reservoir system is the push-pull osmotic pump. These osmotically-controlled delivery systems feature a bi-layer tablet coated with a semi-permeable membrane possessing a laser-bored orifice through which the BC is pushed as aqueous solution is absorbed into the tablet. There are a number of osmotic delivery systems on the market that work via a similar physical principle; these osmotic systems produce very replicable, linear release. Manufacturing this system is definitively non-conventional, requiring specialized equipment and additional processing steps. The inherent complexity of the design adds a corresponding complexity to the development and scale-up of any osmotic membrane product.

The diffusion tablet systems rely on hydrophilic polymer swelling for control of BC release. Polymer systems can be sub-classified as conventional hydrogel systems and modified polymer systems. Conventional hydrogel systems rely upon the penetration of water to form of a gel-like phase through which the bioactive agent is released. These systems often incorporate the BC in a single polymer such as polyethylene oxide or hydroxypropyl methylcellulose. In the case of modified polymer systems, polymers with differing physical characteristics—such as one that is hydrophilic (e.g. HPMC), and one that is pH-dependent in its swelling characteristics, (e.g. pectin)—are combined with the BC. When these polymers interact with dissolution media, a transition phase or interfacial front develops, forming a gradually dissociating semi-solid core surrounded by a gel periphery that allows the BC to be increasingly released as the matrix hydrates. The movement of the dosage form through the gastrointestinal tract, through regions of increasing pH, permits further swelling and erosion of the matrix, culminating in complete release of the BC and complete dissolution of the dosage form.

Prior art formulations cannot deliver beneficial microorganisms over an extended time period or to targeted individual regions of GI tract. Prior art formulations require coating processes to achieve gastric bypass. Further, prior art formulations fail to provide mechanisms for pH control thereby rendering pH sensitive strains much less viable due to variations in GI pH. Further, prior art formulations lack mechanisms of isolating the BC from enzymatic degradation. Prior art formulations lack mechanisms to increase the stability of the dosage form itself through water sequestration of available water. Prior art formulations utilizing dietary fiber as a carrier require too large a volume for efficient oral dosage form manufacture. These and other limitations and problems of the past are solved by the present invention.

SUMMARY

The present invention provides controlled release delivery systems for oral administration of a biological component. Further, a beneficial microorganism is delivered; the probiotic being bacterial in nature.

One embodiment of a controlled delivery system includes a hydrogel or modified matrix formed from an excipient of one or more hydrophilic polymers, polysaccharides, galactomannan gums, resins, polyethylene derivatives or hydrolyzed proteins, either alone or in combination, in which is disposed biological components, in one aspect beneficial microorganisms, and in yet another aspect lyophilized bacteria and their associated lyophilized carrier proteins. Optionally, the delivery system includes one or more additional release modifying excipients (as used herein, the terms "release modifying excipients" and "release modifying agents" are used interchangeably) from the same group of hydrophilic agents for the purpose of attenuating the release of the lyophilized ingredients with pH-specific or enzyme-specific agents, and optionally, one or more physiologically acceptable electrolytic substances included for the purpose of pH control or available water-sequestration.

In another embodiment, the controlled delivery system includes a wax matrix composed of one or more inert insoluble waxes, polymers and/or fillers, alone or in combination, in which is disposed pore forming excipients and the beneficial microorganisms, in one aspect in lyophilized form and their associated lyophilized carrier proteins.

In yet another embodiment of a controlled delivery system includes a multi-particulate system in which a plurality of granules, coated beads or coated non-pareils are distributed within the dosage form in either a simple or an modified polymer matrix or for the purposes of controlled release of beneficial microorganisms, in one aspect in lyophilized form and their associated lyophilized carrier proteins.

In another embodiment, a process for making an extended release dosage form, such as a tablet or capsule, from a pre-blend including mixing a beneficial microorganism with one or more polymers, gums, resins, polyethylene derivatives, or hydrolyzed proteins for the purpose of controlled release; the optional addition of physiologically acceptable electrolytic substances for the purpose of regulating pH within the dosage form; and the optional inclusion of available water-sequestering electrolytic species for the purpose of increasing the stability of the dosage form itself.

In another embodiment of the method of making an extended release dosage form, such a tablet or capsule, includes mixing a beneficial microorganism with a pre-blend of one or more controlling excipients, fillers, desiccants, and flow agents that has been mechanically, chemically, or otherwise dried to reduce the available water present for the purpose of preventing undesirable interactions of the beneficial organisms and hydrophilic agents with any available water within the dosage form.

The system generally includes a hydrophilic agent, an electrolyte, and a biological component (BC), and may optionally include fillers, release modifying agents, desiccants, and flow agents.

In one embodiment, a delivery system for disclosed including a hydrophilic or hydrophobic agent and the BC.

In another embodiment, a delivery system is disclosed including a hydrophilic agent, an electrolytic agent, and the BC.

In yet another embodiment, a delivery system is disclosed including a hydrophilic agent, a release modifying agent, and the BC.

In yet a further embodiment, a delivery system is disclosed including a hydrophobic agent, a release-modifying agent, and a BC.

In yet a further embodiment, a delivery system is disclosed including a hydrophilic agent, a release-modifying agent, and a BC.

In yet a further embodiment, a delivery system is disclosed including a hydrophilic agent, electrolyte, and BC.

In yet a further embodiment, a delivery system is disclosed including a hydrophobic agent, release-modifying agent, electrolyte, and BC.

In yet a further embodiment, a delivery system is disclosed including a hydrophilic agent, release-modifying agent, electrolyte, and BC.

The controlled release formulations for beneficial microorganisms have many advantages over the current art. Targeted delivery of beneficial microorganisms, such as probiotic bacteria, allows for dispersion of probiotic organisms within regions of optimal attachment that may be specific to a given strain or therapeutic goal. One advantage is achieving gastric bypass for the biological contents. Another advantage of the system disclosed is the maintenance of a constant pH within the dosage form surrounding the beneficial microorganisms, allowing an optimal microenvironment for reconstitution of lyophilized ingredients to be created, thereby maximizing viability of the lyophilized ingredients released into the GI tract. Another advantage of the system disclosed is the inclusion of available water-sequestering electrolytic species, an optimal microenvironment may be maintained during storage, thereby increasing the stability of the dosage form itself. Further advantages of the system disclosed are it requires only dry blend and direct compression steps, the system is easily transferable to sites of manufacture and relies on only conventional tableting or encapsulation equipment for production. Because this system is relatively independent of the biological components employed in formulation, targeted delivery of genetically modified bacteria or other beneficial microorganisms is also possible.

One advantage of the present system is the controlled release of the bacteria from the dosage form into the surrounding environment. Another advantage of the present system is the maintenance of a constant pH within the dosage form itself through the use of physiologically acceptable electrolytic substances.

Yet another advantage of the present system is the controlled exposure of the bacteria within the dosage form to aqueous media through controlling the hydration rate of the dosage form via polymer disentanglement.

Yet another advantage of the present system is an increase in the stability of the dosage form and the viability of the contents through the inclusion of available water-sequestering electrolytic species.

Yet another advantage of the present system is its manufacturability: a dry-blend and direct compression form of tablet manufacture and a dry-blend and direct fill form of capsule manufacture. Most advantageous is the absence of any processes which introduce moisture (such as coating or granulation) that may decrease the in vivo viability of the biological component.

The invention will best be understood by reference to the following detailed description of the preferred embodiment. The discussion below is descriptive, illustrative and exemplary and is not to be taken as limiting the scope defined by any appended claims.

DETAILED DESCRIPTION

Figure 1:
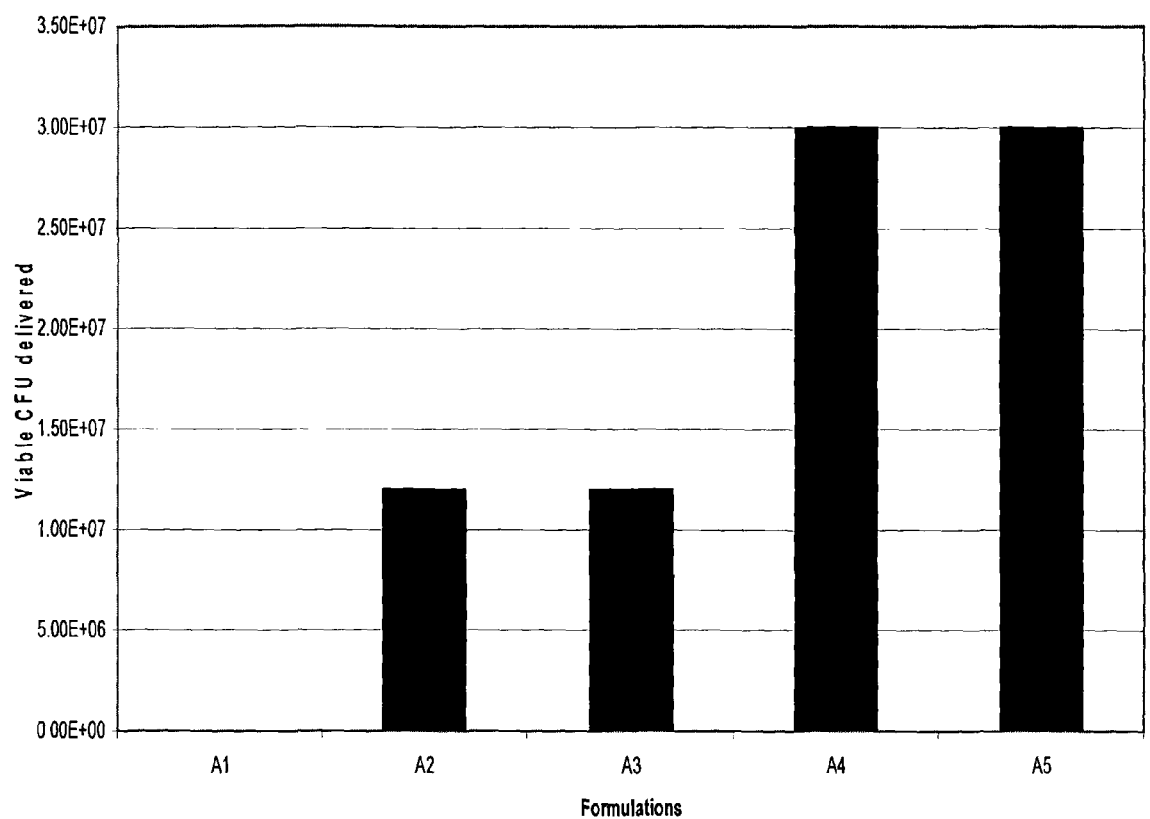
FIG. 1 shows the effects of hydrophilic agents on the controlled release of viable beneficial microorganisms into the small intestine from monolithic tablets.

A delivery system is disclosed for the controlled release of a biological component into the surrounding environment. Controlled release delivery systems include those systems capable of site specific delivery, extended release, sustained release, delayed release, repeat action, prolonged release, bimodal release, pulsitile release, modified delivery, pH sensitive delivery, and/or target specific delivery, among others. The biological components include, but are not limited to, beneficial microorganisms, such as probiotic bacteria. The solid dosage form may take the form of a tablet, capsule, wafer, or sachet, and is not limited to, an orally administered dosage form such as a tablet or capsule.

As used herein, a delivery vehicle, for example a homogenously distributed matrix, is made up of hydrophilic agents and/or a hydrophobic agents. Hydrophilic agents include swelling, viscosity increasing, gel strength enhancing agents. Hydrophobic agents include waxes and other inert materials, such as ethylcellulose or carnauba wax. More particularly, the hydrophilic agent is selected from at least one of the group, but not limited to: a) a starch selected from the group consisting of corn, rice, or potato starch; b) a hydrophilic gum, polysaccharide or galactomannan selected from the group consisting of pectin, agar, dextran, carageenan, tragacanth gum, locust beam gum, acacia gum, guar gum, xanthan gum, ghatti gum, alginic acid or sodium alginate; c) a cellulose derivative selected from the group consisting of methylcellulose, carboxymethylcellulose, sodium starch glycollate, sodium or calcium carboxymethylcellulose, hydroxyethyl methylcellulose, hydroxypropyl methylcellulose, ethylhydroxy ethylcellulose, ethylmethylcellulose, hydroxyethylcellulose, cellulose acetate phthalate or microcrystalline cellulose; d) silica, aluminum silicate, magnesium silicate, aluminum magnesium silicate, sodium silicate or feldspar, e) aluminum hydroxide; f) a protein selected from the group consisting of gelatin or casein; and g) a polymer selected from the group consisting of acrylate, carboxypolymethylene, a polyalkylene glycol or polyvinylpyrrolidone. In one aspect, the hydrophilic polymers are selected from the group of cellulose derivatives such as microcrystalline cellulose (MCC), hydroxypropyl methylcellulose (HPMC), or hydroxypropyl cellulose (HPC), or from gums and polysaccharides such as guar gum or maltodextrin.

As used herein, optionally, the system may include agents added to aid in gastric bypass or modify the release profile of the BC due to pH-specific swelling characteristics or site-specific enzyme degradation within the GI tract. These agents may include but are not limited to at least one of alginate, polysaccharides such as such as gelatin or collagen, guar gum, xanthan gum, pectin, heterogeneous protein mixtures, and polypeptides. The polysaccharides may be pectin and/or an alginate salt, among others. The galactomannan gums may be guar gum, xanthan gum and/or locust bean gum, among others. The polyethylene derivatives may be polyethylene oxide (PEO) and/or polyethylene glycol (PEG), among others. The hydrolyzed proteins may be gelatin and/or collagen, among others. The polypeptides may be gelatin, collagen, casein, or a heterogeneous protein mixture As used herein, BC includes agents such as microbes, DNA, RNA, protein, modified soil organisms (organisms that compete with lactic acid bacteria) bacteria, and biopharmaceuticals. The biological component may be viable or non-viable. The BC may be a beneficial microorganism (or probiotic); and yet in another aspect, the beneficial microorganism is bacterial in nature. The term "probiotic" refers to ingested microorganisms that can live in a host and contribute positively to the host's health and well being.

As used herein, the electrolytes may be at least one of sodium, potassium, or calcium salts, among others (as used herein, the terms "electrolyte" and "electrolytic agent are used interchangeably). Through the inclusion of physiologically acceptable electrolytes, the buffered environment allows reconstitution and release to occur under optimal pH conditions for bacterial viability. The interaction between electrolytes and a hydrophilic agent may allow not only the pH-independent release of the BC, but also allows for the internal pH of the dosage form to remain constant. It is this constant internal pH that contributes significantly to the stability of the biological contents in-vivo.

Optionally, physiologically acceptable salts may be introduced to the bacterial freeze-dried product (FDP) during lyophilization at a ratio of 1.0:0.1 to 1.0:25 bacterial FDP to salt. The system ensures the maintenance of a constant pH within the dosage form itself and acts as a cryoprotectant during the freeze-drying process to prevent lysing of the cell.

As used herein, the system may optionally include a desiccant. The desiccant may include, but is not limited to, sodium carboxymethylcellulose, calcium carboxymethylcellulose, colloidal silica dioxide, and combinations thereof. The disintegration agent may include, but is not limited to, croscarmellose sodium sold as Solutab™ available from Blanver Farmoquimica LTDA and crosprovidone (insoluble polyvinylpyrrolidone) sold as Kollidon CL™ available from BASF.

As used herein, the system may optionally include flow and tubing agents. The flow agents may include, but are not limited to, magnesium stearate and stearic acid.

In a first embodiment, the delivery system includes a swelling hydrophilic agent and a BC. It is based on the homologous distribution of the various components within a solid matrix dosage form. The system allows for a controlled exposure of the BC within the dosage form to an aqueous media by controlling the hydration rate of the dosage form via polymer disentanglement and matrix erosion. Optionally, the system may also include a physiologically acceptable electrolyte, a release modifying excipient such as a gum or polysaccharide, a desiccant, and flow or tubing agents, alone or in combination. Electrolytes can provide a mechanism for available water-sequestration to increased stability of the dosage form and the viability of its contents. Desiccants may also be used to sequester available water for a similar purpose. Release modifying excipients, such as gums and polysaccharides, may be used to induce site-specific release through pH-specific swelling or site-specific enzymatic degradation. Flow or tubing agents may be used to improve the manufacturability. This may also result in decreased loss of viability during manufacture due to compression and heat resulting from powder flow, tableting, and encapsulation.

In one aspect of the embodiment, the BC may be a probiotic pre-blend, which can be blended with a carrier. The carrier may be, but is not limited to, monosaccharides or polysaccharides, such as maltodextrin, swellable polymers, such as hydroxypropyl methylcellulose, inert fillers, such as microcrystalline cellulose or di-calcium phosphate, or other inert substances, such as carnauba wax. In the aspect wherein a carrier is included, the carrier may function to assist in the controlled release of the BC, to aid in the manufacturability of the dosage form, or to increase the stability of the dosage form.

The delivery system can be a readily manufacturable solid dosage form. In one aspect, the dosage form is in the form of a monolithic tablet or capsule. When a tablet or capsule, it may be administered orally, anally, and vaginally, among other routes. In one aspect, the dosage form is a monolithic tablet created from a direct-compressible dry blend which does not require processes, such as enteric coating, granulation, or spray drying, that expose the BC to temperatures that might cause any biological contents to be damaged. However, provided such coating or granulation processes are carried out in a manner that do not damage the biological contents, nor adversely affect the hydration state of the matrix, they may be amenable.

Release of the biologic into the surrounding environment may be accomplished through a rate-controlled hydration and subsequent swelling of hydrophilic agents. The release of the biologic is determined by the erosion rate and polymeric disentanglement of the swollen hydrophilic matrix. Without subscribing to a particular theory of kinetics, the swelling of the hydrophilic matrix is retarded by a plurality of layers of viscous gelled hydrophilic agents; these gel-states result from the interaction of the hydrophilic agents with the penetrating gastrointestinal fluid. While primarily erosion dependent, the gradual hydration and gelling reaction within the hydrophilic matrix allows for a highly reproducible, programmable release pattern. The programmability of the system allows for nearly any physiologically relevant release pattern to be accomplished. Mathematical treatment of the hydrophilic matrix swelling, erosion, and ensuing release of BC can be determined, though each model will be representative of the particular components specific to each formulation. This can be accomplished without the need for undue experimentation. Formulation specific to the physical characteristics of each BC and the desired release profile can be accomplished through both theoretical and empirical means, allowing dissolution of the system and BC release to occur in a specific physiologic region. Release of contents in a given region of the GI tract is accomplished by the slowly hydrating hydrophilic matrix containing the biological actives segregated from the external environment until the desired physiologic region of release, which may be employed to achieve gastric bypass. Consideration of both the area and duration of release is essential in formulation so as to program the system with an appropriate ratio of components to ensure the desired release profile.

The homologous distribution of BCs within the hydrophilic matrix provides protection from the fluctuations in pH and exposure to enzymatic degradation present in external environment. When lyophilized microorganisms are delivered, this isolation from the outside environment allows the bacteria to remain in lyophilized stasis significantly longer than with conventional immediate release dosage forms.

In another embodiment, when physiologically acceptable electrolytes are included into the delivery system, the electrolyte maintains an intra-dosage form pH irrespective of the external pH. This internal pH may be modified through the selection of electrolytes that are both physiologically-acceptable for human consumption and physiologically-appropriate to individual BCs. When delivering lyophilized beneficial microorganisms, this internal pH may be selected to create an optimal environment for the reconstitution of the lyophilized organisms. Such an environment may result in an increase in viability during the reconstitution process, and moreover, may limit the exposure of the lyophilized microorganism to fluctuations in gastrointestinal pH, resulting in an increase in organism viability while the matrix is in a hydrated state and prior to the organisms release into the environment.

The addition of physiologically-acceptable electrolytes may also be employed to aid in available water-sequestration. When delivering lyophilized beneficial microorganisms, this is especially useful, as interactions with any available water—such as the available water present in the constituent controlling excipients, flow agents and desiccants—may result in inadvertent, premature reconstitution prior to release in the gastrointestinal environment. Premature reconstitution from a lyophilized state causes the organisms to begin metabolizing available sources of energy; the constituents of the delivery system provide very limited sources of energy and when these locally available sources of energy are exhausted, the organisms expire. The metabolic byproducts of prematurely reanimated organisms may also have a negative impact on the viability of the remaining, non-reanimated organisms. When disposed in a homogeneous manner throughout the dosage form, electrolytic substances that have a higher degree of hydrophilicity than the other constituents of the delivery system surrounding them may preferentially hydrate, decreasing or preventing the re-hydration of the lyophilized agents. An example of a system not including an electrolyte is a system that is dependent upon erosion as its release mechanism, or one in which the maintenance of a constant pH within the dosage form is not desired; lyophilized beneficial microorganisms and hydrophilic agents do not require an electrolyte to make a controlled release dosage form capsule. Another example that does not require an electrolyte is where the controlled release of non-viable beneficial microorganisms (such as non-viable bacterial biomass) is sought as the primary function of the dosage form.

In another embodiment of the delivery system, the addition of release modifying excipients, such as hydrophilic polymers or gums demonstrating pH or enzyme sensitivity, may be employed to alter the swelling or erosion characteristics of the matrix, such as the initiation of swelling or the rate of erosion of the matrix. These release modifying excipients function in combination with the hydrophilic agent to control the release of the biological component. These excipients may be employed to reduce the amount of exposure to the gastric environment by reducing matrix swelling during exposure to gastric pH or during the time the dosage form is expected to transit through the stomach and pylorus. These release modifying excipients may be selected for their in vivo degradation characteristics that occur in localized regions of the gastrointestinal tract. The release modifying agent, when used alone, may function as the hydrophilic agent. One example of this, among many, is that pectin mainly breaks down at the higher pH and enzyme rich environment of the large intestine, thus it can be employed alone as the hydrophilic agent if a greater proportion of lower intestinal tract delivery was desired. Another example among others it that gelatin largely breaks down in the small intestine. With regards to pharmaceutical controlled release formulations, the location of polymer breakdown is of special significance as bioavailability is determined by the amount of drug released within a given timeframe relative to a physiological site of absorption specific to that type of compound. The delivery of biological components is essentially similar in intent, given localized sites for absorption and adsorption. When delivering beneficial microorganisms, the inclusion of release modifying excipients whose swelling characteristics are pH dependent, specifically compounds that preferentially swell in environments above pH 1.0-1.5, is useful for the delivery of lactic acid bacteria that are susceptible to viability losses when exposed to low pH. The low-pH environment will inhibit swelling, thus retarding both beneficial microorganism release and acid-penetration into the dosage form. The inclusion of release modifying excipients whose erosion is enzyme-dependent, specifically compounds that degrade preferentially in the presence of lower intestinal tract enzymes, is useful for the delivery of lactic acid bacteria whose attachment site is distal to the location of the enzymes.

In another embodiment of the delivery system, the system is a pore-forming wax matrix composed of one or more inert insoluble waxes, polymers or fillers in which is disposed pore forming excipients and the active lyophilized bacteria and their associated lyophilized carrier proteins. Hydrophilic agents may be included with hydrophobic agents to make pore forming wax matrices.

In yet another embodiment, the system may include a multi-particulate plurality of granules, coated beads or coated non-pareils are distributed within the dosage form in either an active polymer matrix or immediate release matrix for the purposes of controlled release of the lyophilized active ingredients.

In one embodiment, the dosage form disclosed is formed from a pre-blend. When a monolithic tablet, the pre-blend is mixed using dry-blend techniques known to those skilled in the art, and the dosage form is created using a direct compression process. Employing a pre-blend that is formed using dry-blend techniques is a significant improvement over the use of blends resulting from granulation, spheronization-extrusion, or other processes that might expose the biological components to moisture or solvents and potentially lower the viability of the biological components. Employing a pre-blend that is capable of forming a monolithic dosage form using only the techniques of direct-compression, in the case of a tablet, or high speed encapsulation, in the case of a capsule, is a significant improvement over manufacturing processes that require multi-stage compression, multiple geometrically-altered components or coatings that might expose the biological component to hazardous environmental conditions such as solvents, high forces of compression, excessive heat or undue physical stress. When delivering lyophilized beneficial microorganisms, preventing the premature reconstitution of the organisms is important to maintaining the in vivo viability of the organisms.

The dosage form disclosed may be formed from a pre-blend in which a lyophilized biological component, for example a lyophilized beneficial microorganism, is mixed with a pre-blend of one or more controlling excipients, fillers, desiccants, and flow agents that has been mechanically, chemically, or otherwise dried to reduce the available water present for the purpose of preventing undesirable interactions of the beneficial organisms and hydrophilic agents with any available water within the dosage form. The minimization of available water within the dosage form is intended to prevent unintentional or pre-mature reconstitution of the lyophilized organisms. The use of a pre-blend in which the non-lyophilized components are dried and subsequently blended with the lyophilized components, while not necessary for the creation of a controlled release dosage form, is a significant improvement over the use of either non-dried excipients that may contain enough available water to induce pre-mature reconstitution prior to in vivo release, or the drying of a pre-blend containing both lyophilized and non-lyophilized components, which exposes the lyophilized components to undue heat and may extensively reduce their in vivo viability.

Unless otherwise noted, all of the following embodiments are formulated through standard dry blend and directly compression with an appropriate lubricant such as magnesium stearate or stearic acid.

In the first embodiment, a formulation is disclosed combining the bacterial lyophilized (freeze-dried) powder pre-blend (FDP) with a suitable hydrophilic agent such as HPMC, MCC, or PEO, in a ratio of about 1.0:0.1 to 1:25 FDP to hydrophilic agent.

In the second embodiment, a formulation is disclosed including bacterial FDP, hydrophilic agent, and a physiologically acceptable electrolyte such as $NaHCO_3$, $Na2 CO_3$, or $Ca CO_3$, in a ratio of about 1.0:0.1:0.1 to 1:25:25 FDP to hydrophilic agent to electrolyte.

The third embodiment, a formulation is disclosed including bacterial FDP, a hydrophilic agent, and a release modifying agent in the form of a hydrophilic polysaccharide such as pectin, sodium alginate alginic acid, or a gum such as xanthan gum, guar gum, locust bean gum, or tragacanth gum, in a ratio of about 1.0:0.1:0.1 to 1:25:25 FDP to hydrophilic agent to polysaccharide or gum.

The fourth embodiment, a formulation is disclosed including bacterial FDP, a hydrophilic agent, a release modifying agent in the form of a hydrophilic polysaccharide or gum, and a physiologically acceptable salt in a ratio of about 1.0:0.1:0.1:0.1 to 1:25:25:25 FDP to hydrophilic agent to polysaccharide or gum to electrolyte.

The fifth embodiment, a formulation is disclosed including bacterial FDP, a hydrophilic agent, a release modifying agent in the form of a hydrophilic polysaccharide or gum, a physiologically acceptable salt, and an inert filler in a ratio of about 1.0:0.1:0.1:0.1:0.1 to 1:25:25:25:25 FDP to hydrophilic agent to polysaccharide or gum to electrolyte to inert filler.

In the sixth embodiment, a formulation is disclosed combining the lyophilized lactic acid bacteria pre-blend with a suitable hydrophobic agent such as carnauba wax, in a ratio of about 1.0:0.1 to 1:25 FDP to hydrophobic agent.

In the seventh embodiment, a formulation is disclosed including bacterial FDP, a hydrophobic agent, and a physiologically acceptable electrolyte such as $NaHCO_3$, $Na2 CO_3$, or $Ca CO_3$, in a ratio of about 1.0:0.1:0.1 to 1:25:25 FDP to hydrophobic agent to electrolyte.

The eighth embodiment, a formulation is disclosed including bacterial FDP, a hydrophobic agent, a physiologically acceptable electrolyte such as $NaHCO_3$, $Na2 CO_3$, or $Ca CO_3$, and a release modifying agent in the form of a hydrophilic polysaccharide such as pectin, sodium alginate alginic acid, or a gum such as xanthan gum, guar gum, locust bean gum, or tragacanth gum, in a ratio of about 1.0:0.1:0.1:0.1 to 1:25:25:25 FDP to hydrophobic agent to polysaccharide or gum to electrolyte.

The dosage forms may be monolithic tablets or gelatin or vegetable capsules for oral, anal, or vaginal delivery.

Methods

The formulations described below have been prepared in accordance with the following methods. In these formulations, tablets were prepared using a method of dry blending and direct compression using a Carver hydraulic press or a rotary tablet press. Evaluations were performed using a USP Type II (paddle) dissolution apparatus.

Examples 1-5, 9, 10, and 12 were conducted by exposing the dosages to 1000 mL 0.1N HCl for 2 hours at 50 RPM. The dosages were then removed and placed into peptone buffer medium and stomached, (the dosage form is crushed and homogenized within the buffer media for the purpose of enumerating the remaining bacteria in the tablet), after which a sample was taken from the dissolution media. The samples were then plated on MRS and RCM media to discern viable colony forming units (CFU).

Example 6 was performed by exposing the dosages to 1000 mL USP HCl for 2 hours at 50 RPM. The dosages were removed and placed into $KH_2PO_4$ buffer dissolution medium and the dissolution media was sampled at regular intervals. The samples were then plated on MRS and RCM media to discern viable colony forming units (CFU).

Examples 7 and 8 were performed by exposing the dosages to 1000 mL USP HCl (Ex. 7) or 0.1N HCl (Ex. 8) for 2 hours at 50 RPM. The dosage forms were removed and placed into $KH_2PO_4$ (Ex 7) or peptone (Ex. 8) buffer medium and the dissolution media was sampled at regular intervals. The samples were then filtered, reacted with 4',6-diamidino-2-phenylindole, and enumerated under UV-light.

Example 11 was performed using tablets produced from excipients desiccated in a fluid bed drier, mixed with the lactic acid bacteria pre-blend and flow agents, and tableted. The dosage forms were then exposed to 1000 mL 0.1N HCl for 2 hours at 50 RPM. The dosages were removed and placed into peptone buffer medium and stomached, after which the dissolution media was sampled. The samples were then plated on MRS and RCM media to discern viable colony forming units (CFU).

Example 13 was performed using dosages packaged in foil sachets and exposed to ambient environmental conditions (25 degrees C., 60% Relative Humidity) for 4 months and subsequently tested. The samples were removed to peptone buffer solution, stomached, and plated on MRS and RCM media to discern viable colony forming units (CFU).

Example 1

A monolithic tablet of approximately 382 mg having a hydrophilic agent and biological component (BC) was prepared as shown in Table 1, with the group A1 as the control group. In this example, the beneficial microorganism is the lactic acid bacteria pre-blend of lyophilized powder and starch, and the hydrophilic agent employed is microcrystalline cellulose (MCC), maltodextrin, hydroxypropyl methylcellulose (HPMC), or polyethylene oxide (PEO). The addition of the hydrophilic agent will retard the release of the BC from the dosage form. Stearic acid is included as a flow agent and silica is employed as flow agent and desiccant.

As shown in FIG. 1, the results of this example reflect a level of controlled release granted through the use of a matrix comprised of a hydrophilic agent and a lyophilized BC. This controlled release is shown through a much higher level of viable lactic acid bacteria colony forming units (CFU) delivered after exposure to gastric media than the control. The use of less swellable hydrophilic agents such as MCC and maltodextrin are associated with sufficient, but lower levels of control. A superior level of control is demonstrated in both polyethylene oxide and HPMC matrices. Thus, the hydrophilic agent is not limited to a particular type of hydrophilic agent, so long as sufficient matrix viscosity is achieved.

TABLE 1

| Dosage Formulas (mg) | A1 (CTRL) | A2 | A3 | A4 | A5 |
|---|---|---|---|---|---|
| Lactic acid bacteria pre-blend | 150 | 150 | 150 | 150 | 150 |
| HPMC | 0 | 0 | 0 | 200 | 0 |
| PEO | 0 | 0 | 0 | 0 | 200 |
| MCC | 0 | 200 | 0 | 0 | 0 |
| Maltodextrin | 0 | 0 | 200 | 0 | 0 |
| Stearic Acid | 16 | 16 | 16 | 16 | 16 |
| Silica | 16 | 16 | 16 | 16 | 16 |
| TOTAL WEIGHT | 182 | 382 | 382 | 382 | 382 |

Example 2

A monolithic tablet of approximately 382 mg containing a hydrophilic agent, an electrolytic agent, and a biological component was prepared as set forth in Table 2, with B1 as the control group. The formulation employs HPMC as the hydrophilic agent, $NaHCO_3$, $Na_2CO_3$ or $NaH_2PO_4$ as the electrolytic agent, and the lactic acid bacteria pre-blend of lyophilized powder and starch as the biological component (BC). The addition of $NaHCO_3$, $Na_2CO_3$ or $NaH_2PO_4$ establishes the pH within the dosage form. Stearic acid is included as a flow agent and silica is employed as flow agent and desiccant.

Figure 2:
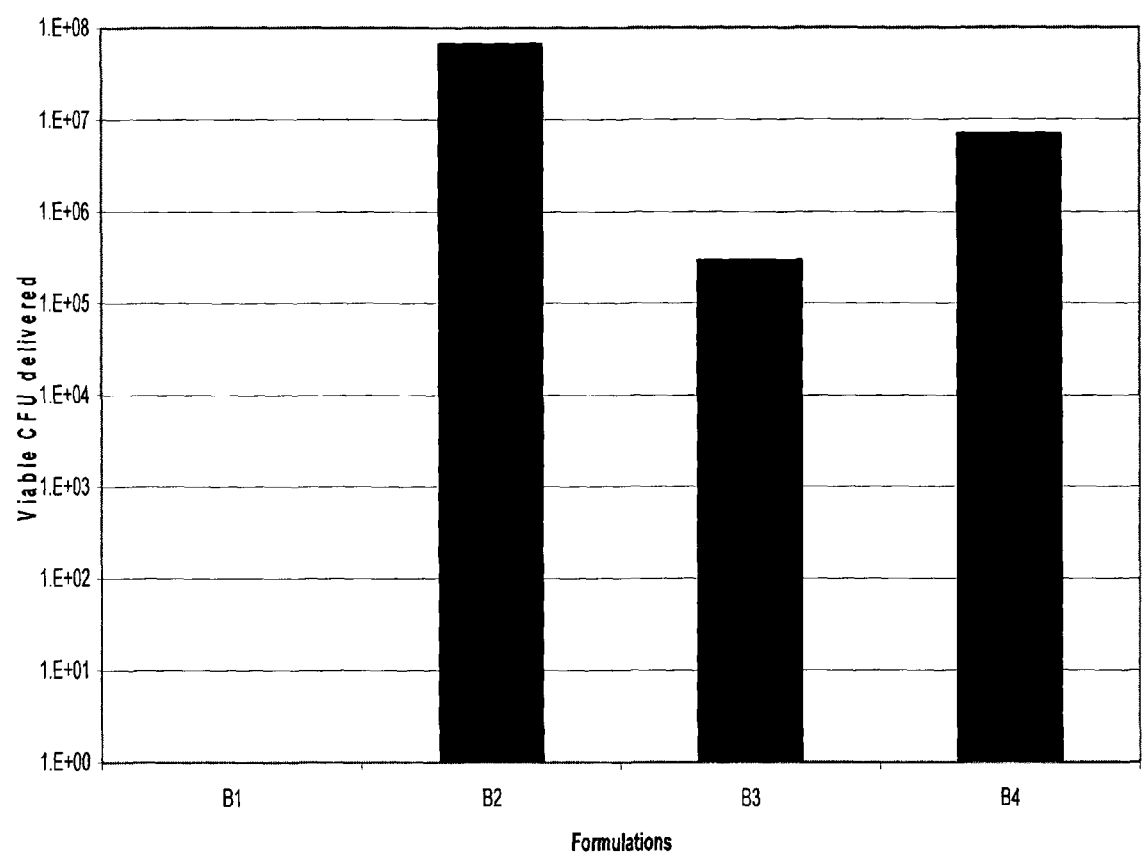
FIG. 2 shows the effects of the addition of electrolytes on the controlled release of viable beneficial microorganisms into the small intestine from monolithic tablets.

This example demonstrates, as shown in FIG. 2, that the internal pH of the dosage form is altered by the presence of an electrolyte, affecting the amount of viable CFU delivered. This establishment of a particular internal pH is associated with differing levels of viability for a given reconstituted lyophilized organism. In particular, formulation B2, which contains $Na_2CO_3$, provides an internal pH which aides in the reconstitution of viable lactic acid bacteria.

TABLE 2

| Dosage Formulas (mg) | B1 (ctrl) | B2 | B3 | B4 |
|---|---|---|---|---|
| Lactic acid bacteria pre-blend | 150 | 150 | 150 | 150 |
| HPMC | 00 | 100 | 100 | 100 |
| $NaHCO_3$ | 0 | 100 | 0 | 0 |
| $NaHCO_3$ | 0 | 0 | 100 | 0 |
| $NaH_2PO_4$ | 0 | 0 | 0 | 100 |
| Stearic acid | 16 | 16 | 16 | 16 |
| Silica | 16 | 16 | 16 | 16 |
| Total Weight | 182 | 382 | 382 | 382 |

Example 3

A monolithic tablet of approximately 382 mg containing a hydrophilic agent, a release-modifying excipient, and a BC was prepared as shown in Table 3, with C1 as the control group. The hydrophilic agent employed is HPMC, the release-modifying excipient employed is pectin or gelatin, and the lactic acid bacteria pre-blend of lyophilized powder and starch is the BC. Stearic acid is included as a flow agent and silica is employed as flow agent and desiccant.

Figure 3:
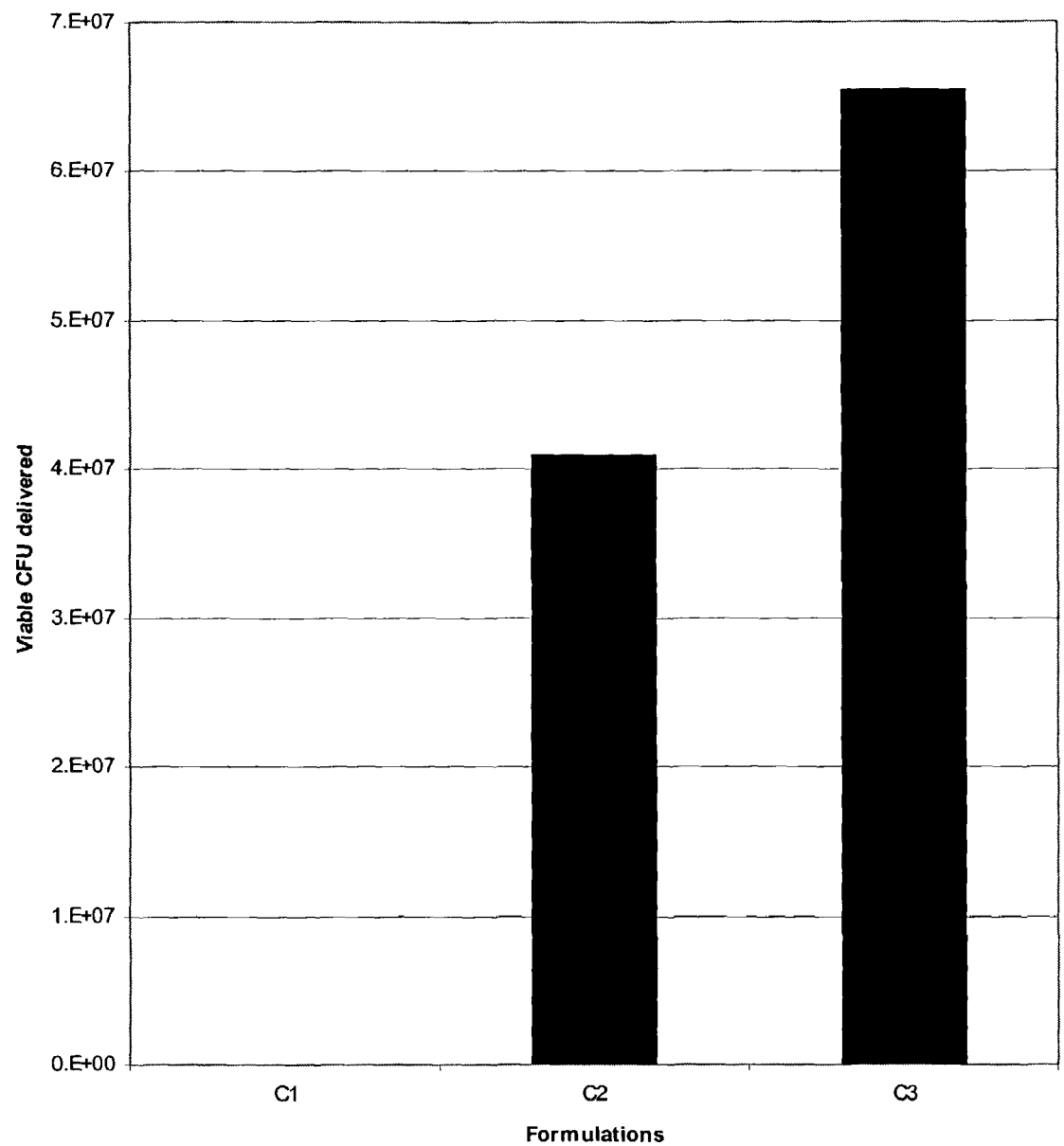
FIG. 3 shows the effects of the addition of pH- and enzyme-sensitive agents on the controlled release of viable beneficial microorganisms into the small intestine from monolithic tablets.

This example illustrates, as shown in FIG. 3, an increased level of control possible when release modifying excipients are added to a hydrophilic swellable matrix. The presence of pectin or gelatin is associated with a degree of pH-dependent degradation and an overall increase in matrix viscosity which retards the release of the BC. This is reflected in the increase in viable CFU delivered after exposure to gastric pH.

TABLE 3

| Dosage Formulas (mg) | C1 (CTRL) | C2 | C3 |
|---|---|---|---|
| Lactic acid bacteria pre-blend | 150 | 150 | 150 |
| HPMC | 0 | 100 | 100 |
| Pectin | 0 | 100 | 0 |
| Gelatin | 0 | 0 | 100 |
| Stearic acid | 16 | 16 | 16 |
| Silica | 16 | 16 | 16 |
| TOTAL WEIGHT | 182 | 382 | 382 |

Example 4

A monolithic tablet of approximately 382 mg containing a hydrophilic agent and a BC was prepared as shown in Table 4 with C1 as the control group. The hydrophilic agent employed is pectin and the lactic acid bacteria pre-blend of lyophilized powder and starch is the BC. Stearic acid is included as a flow agent and silica is employed as flow agent and desiccant.

Figure 4:
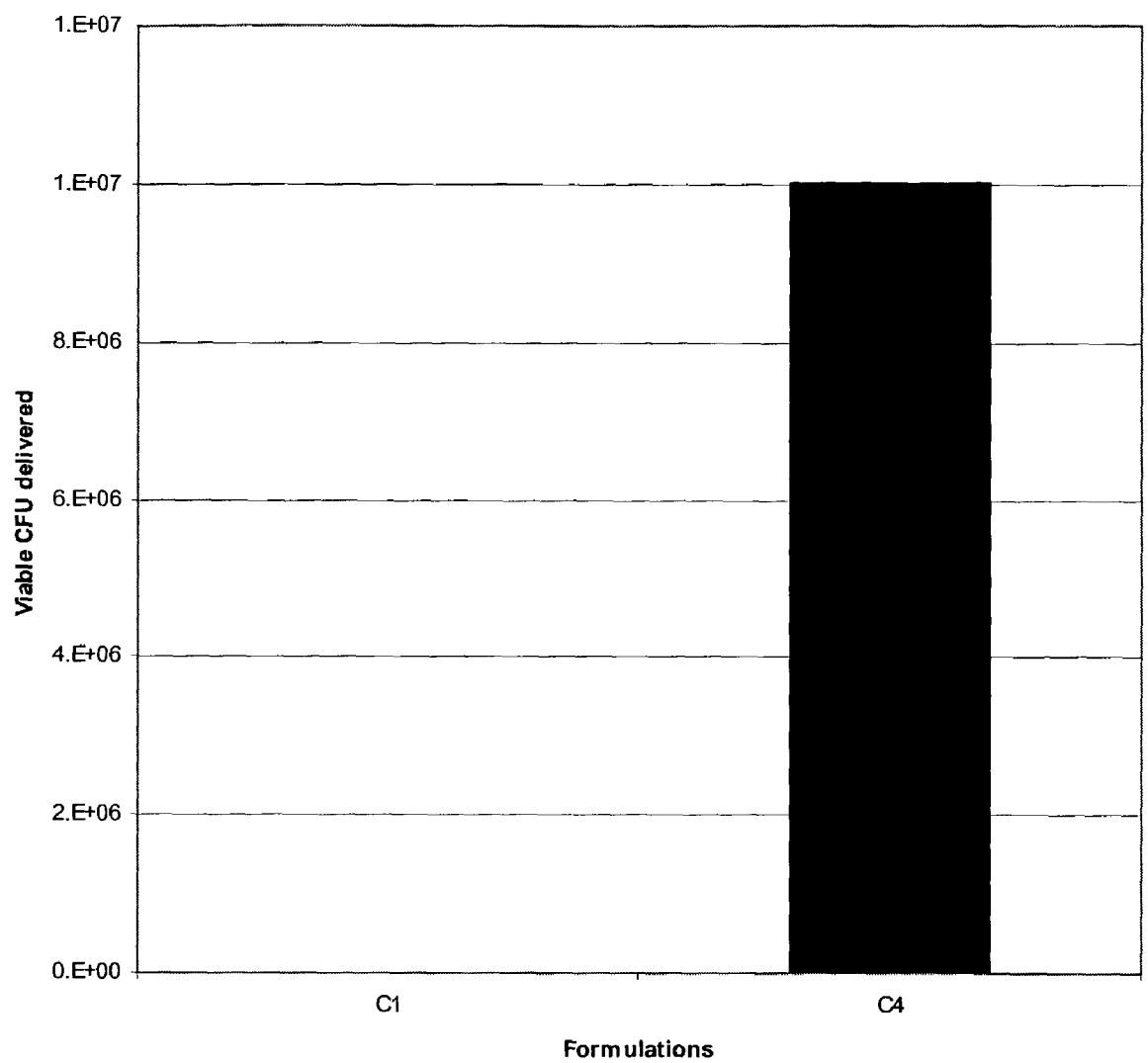
FIG. 4 shows the effects of the addition of pH- and enzyme-sensitive agents on the controlled release of viable beneficial microorganisms into the small intestine from monolithic tablets.

This example illustrates, as shown in FIG. 4, a level of control possible when employing a hydrophilic agent that displays pH-dependent and enzyme-dependent degradation. This example also illustrates the use of a release-modifying agent as a hydrophilic agent. The presence of pectin is also associated with an overall increase in matrix viscosity which retards the release of the BC. This is reflected in the increase in viable CFU delivered after exposure to gastric pH.

TABLE 4

| Dosage Formulas (mg) | C1 (CTRL) | C4 |
|---|---|---|
| Lactic acid bacteria pre-blend | 150 | 150 |
| Pectin | 0 | 200 |
| Stearic acid | 16 | 16 |
| Silica | 16 | 16 |
| TOTAL WEIGHT | 182 | 382 |

Example 5

A monolithic tablet of approximately 482 mg containing a hydrophilic agent, a release-modifying excipient, an electrolytic agent, and a BC was prepared as shown in Table 5 with D1 as the control group. The hydrophilic agent employed is guar gum, the release-modifying excipient employed is pectin, the electrolytic agent is $NaHCO_3$, and the lactic acid bacteria pre-blend of lyophilized powder and starch is the BC. Stearic acid is included as a flow agent and silica is employed as flow agent and desiccant.

Figure 5:
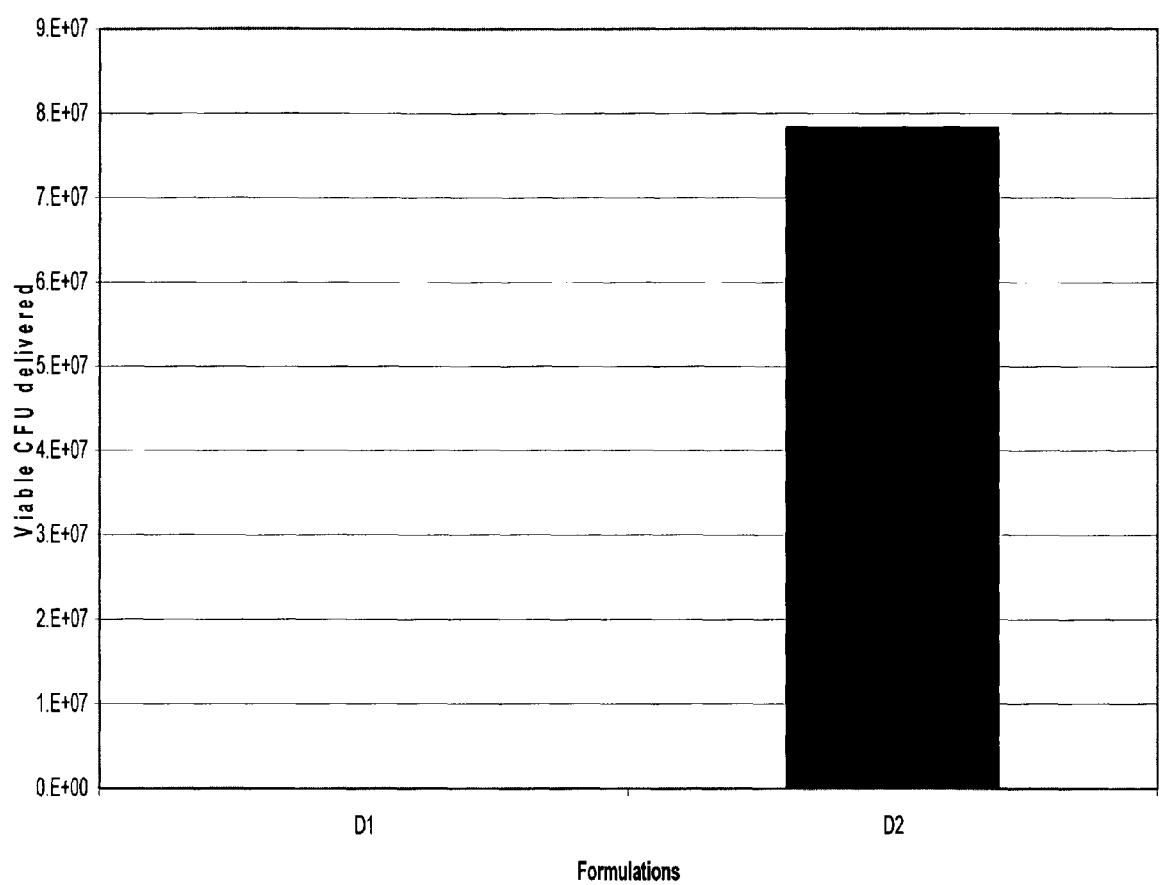
FIG. 5 shows the effects of electrolytes and pH- and enzyme-sensitive agents on the controlled release of viable beneficial microorganisms into the small intestine from monolithic tablets.

This example illustrates, as shown in FIG. 5, the application of galactomannan gum as a hydrophilic agent in combination with a sodium salt and a polysaccharide in a hydrophilic swellable matrix. The presence of a galactomannan gum is associated with an overall increase in matrix viscosity which retards the release of the BC, and the presence of NaHCO$_3$ is associated with internal pH modulation favorable to the reconstitution of lactic acid bacteria. This is reflected in the increase in viable lactic acid CFU delivered after exposure to gastric pH.

TABLE 5

| Dosage Formulas (mg) | D1 (CTRL) | D2 |
| --- | --- | --- |
| Lactic acid bacteria pre-blend | 150 | 150 |
| Guar | 0 | 100 |
| NaHCO$_3$ | 0 | 100 |
| Pectin | 0 | 100 |
| Stearic acid | 16 | 16 |
| Silica | 16 | 16 |
| TOTAL WEIGHT | 182 | 482 |

Example 6

A monolithic tablet of approximately 443 mg containing a hydrophilic agent, an electrolytic agent, a release-modifying excipient, a filler, and a BC was prepared as shown in Table 6. The hydrophilic polymer employed is HPMC, the electrolytic agent is NaHCO$_3$, the release-modifying excipient employed is pectin, the filler employed is MCC and the lactic acid bacteria pre-blend of lyophilized powder and starch is the BC. The addition of inert filler is associated with increased power flowability, which is often advantageous during manufacture. Stearic acid is included as a flow agent and silica is employed as flow agent and desiccant. Turmeric is included as a colorant.

Figure 6:
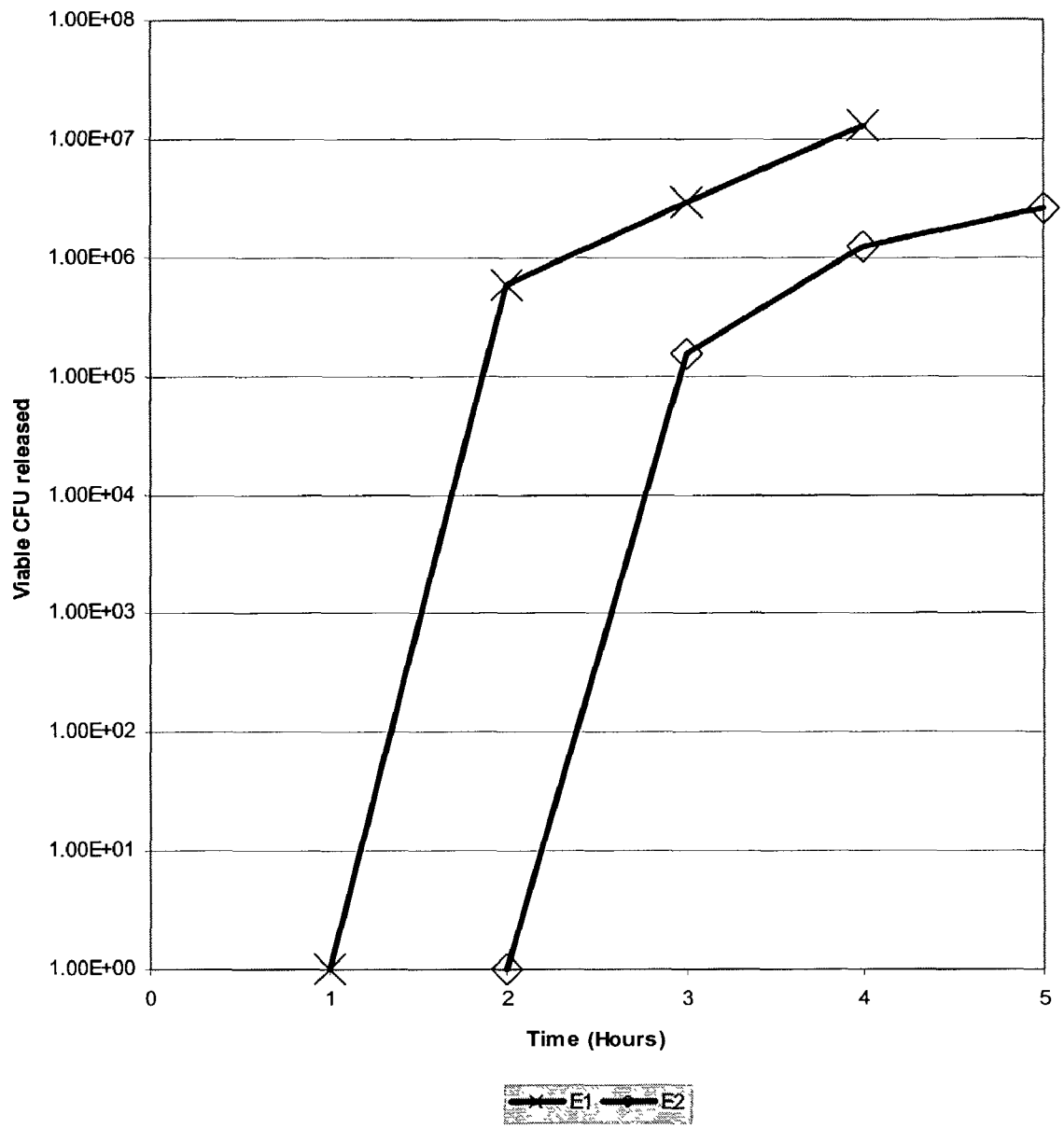
FIG. 6 shows the capacity for the controlled release of viable beneficial microorganisms over extended durations from monolithic tablets.

As depicted in FIG. 6, the results of this example demonstrate the capacity for the controlled release of viable BCs over an extended duration. The controlled release of the hydrophilic matrix is also shown to perform similarly regardless of the duration of exposure to gastric media; E1 and E2 are identical formulations showing the difference in release based upon a 1 hour, or 2 hour exposure time, respectively.

TABLE 6

| Dosage Formulas (mg) | E1 | E2 |
| --- | --- | --- |
| Lactic acid bacteria pre-blend | 150 | 150 |
| HPMC | 50 | 50 |
| NaHCO$_3$ | 50 | 50 |
| MCC | 200 | 200 |
| Pectin | 50 | 50 |
| Stearic acid | 16 | 16 |
| Silica | 16 | 16 |
| Turmeric | 2 | 2 |
| TOTAL WEIGHT | 443 | 443 |

Example 7

A monolithic tablet of approximately 443 mg containing a hydrophilic agent, an electrolytic agent, a release-modifying excipient, a filler, and a BC was prepared as shown in Table 6.

Figure 7:
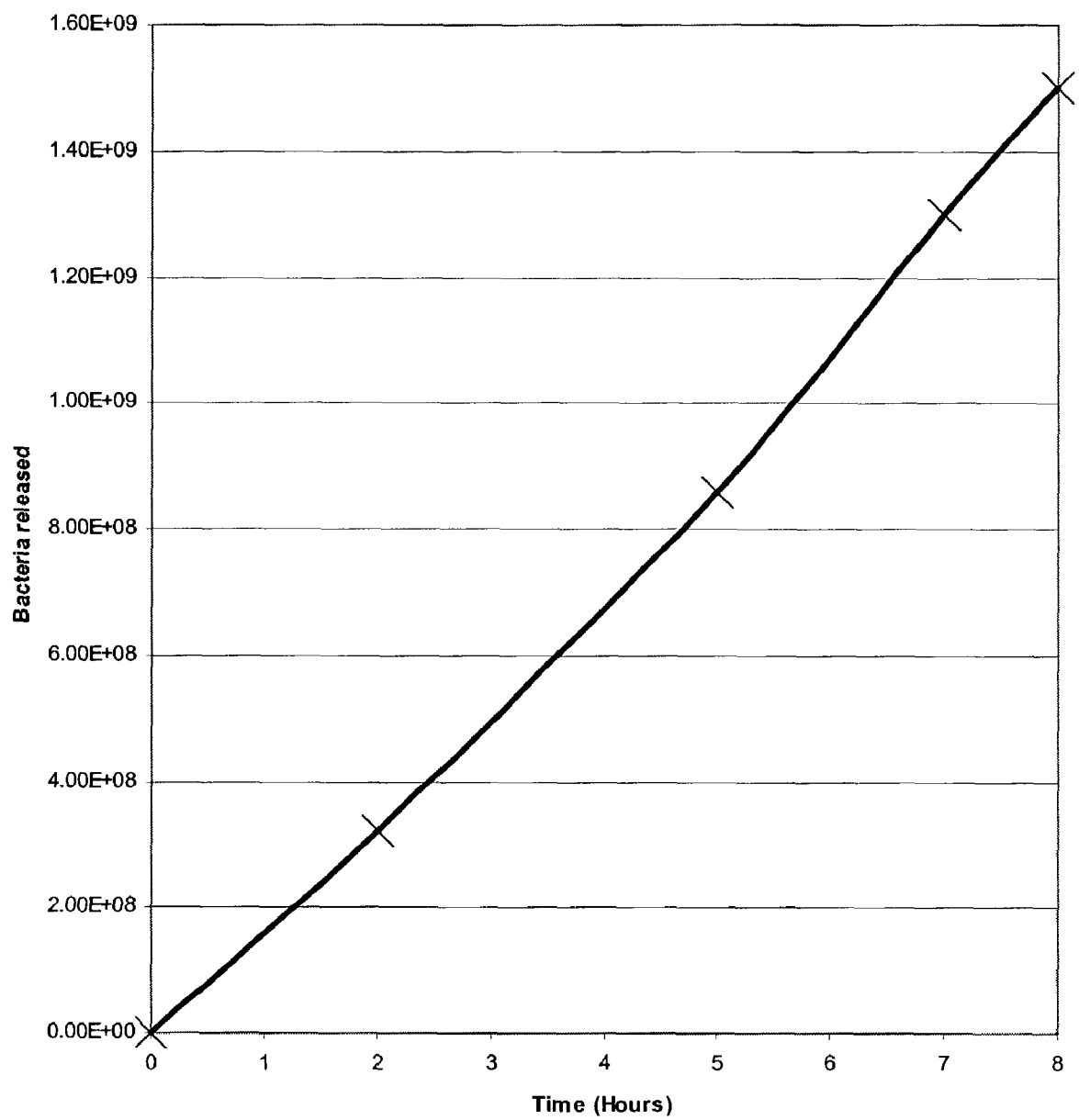
FIG. 7 shows the controlled release of beneficial microorganisms over an extended duration of 8 hours from monolithic tablets.

As depicted in FIG. 7, the results of this example demonstrate the capacity for the controlled release of bacteria over an extended duration, for example, from zero to eight hours. The rate of release is linear from zero until approximately 8 hours.

Example 8

A monolithic tablet of approximately 532 mg containing a hydrophilic agent, an electrolytic agent, a release-modifying excipient, a filler, and a BC was prepared as shown in Table 8. The hydrophilic agent employed is HPMC or PEO, the electrolytic agent is NaHCO$_3$, the release-modifying excipient employed is pectin, the filler employed is MCC and the *bifidobacterium* pre-blend of lyophilized powder and starch is the BC. Stearic acid is included as a flow agent and silica is employed as flow agent and desiccant. Turmeric is included as a colorant.

Figure 8:
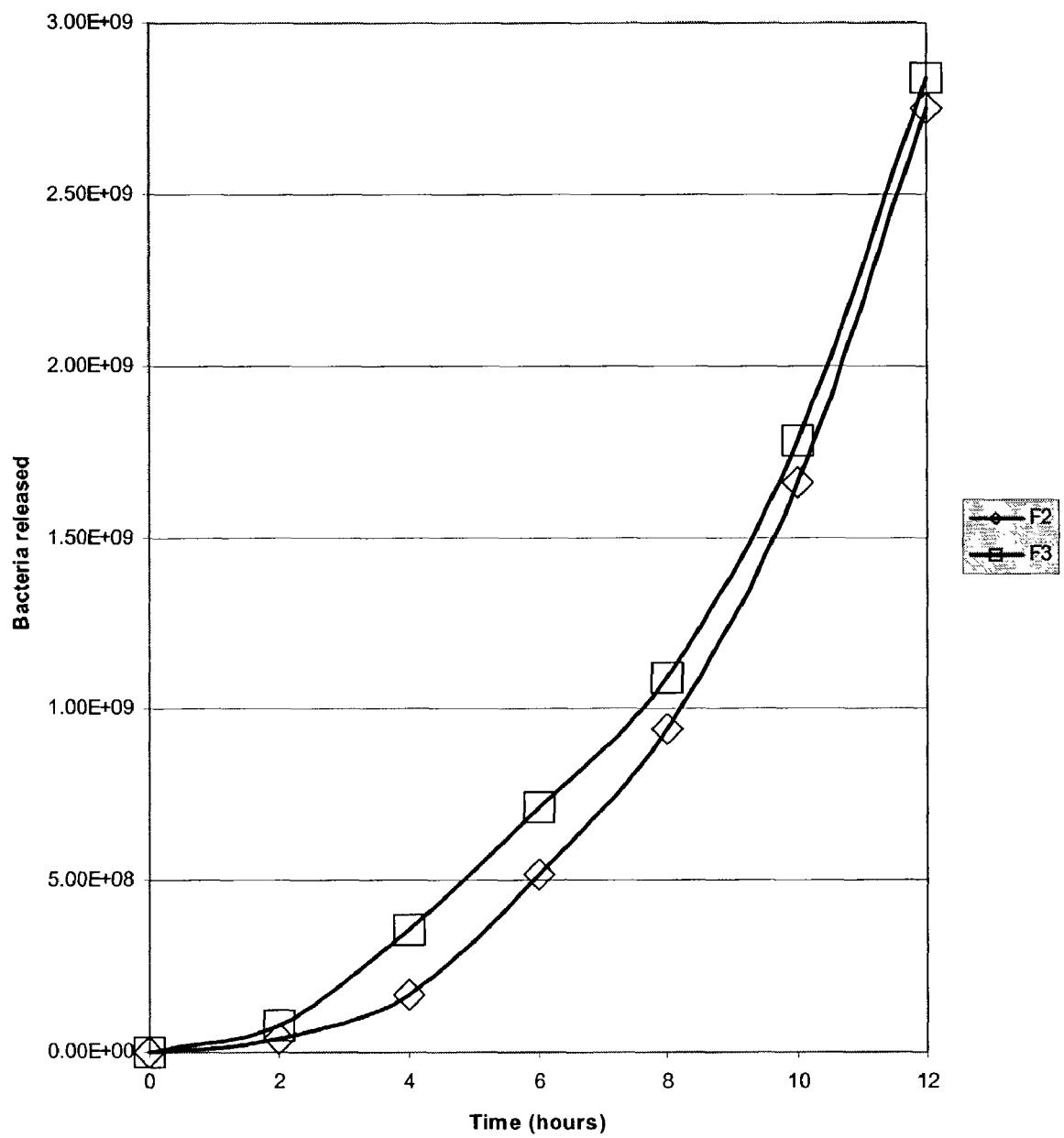
FIG. 8 shows the controlled release of beneficial microorganisms specific to the lower intestinal tract over an extended duration of 12 hours from monolithic tablets.

As depicted in FIG. 8, the results of this example demonstrate the capacity for the controlled release of BCs over an extended duration. The controlled release of the hydrophilic matrix is also shown to release in a profile favorable for the delivery of bacteria after eight hours. Such an example would be useful to delivering the bacteria to the lower intestine and beyond.

TABLE 8

| Dosage Formulas (mg) | F2 | F3 |
| --- | --- | --- |
| Bifidobacterium bacteria pre-blend | 150 | 150 |
| HPMC | 150 | 0 |
| PEO | 0 | 150 |
| Pectin | 100 | 100 |
| NaHCO$_3$ | 100 | 100 |
| Stearic acid | 16 | 16 |
| Silica | 16 | 16 |
| TOTAL WEIGHT | 532 | 532 |

Example 9

Two-piece capsules of approximately 665 mg containing two hydrophilic agents, an electrolytic agent, a release-modifying excipient, and a BC was prepared as shown in Table 9 with G1 as the control group. The hydrophilic agents employed are HPMC and Guar, the electrolytic agent is NaHCO$_3$, the release-modifying excipient employed is pectin and the lactic acid bacteria pre-blend of lyophilized powder and starch is the BC. Stearic acid is included as a flow agent and silica is employed as flow agent and desiccant.

Figure 9:
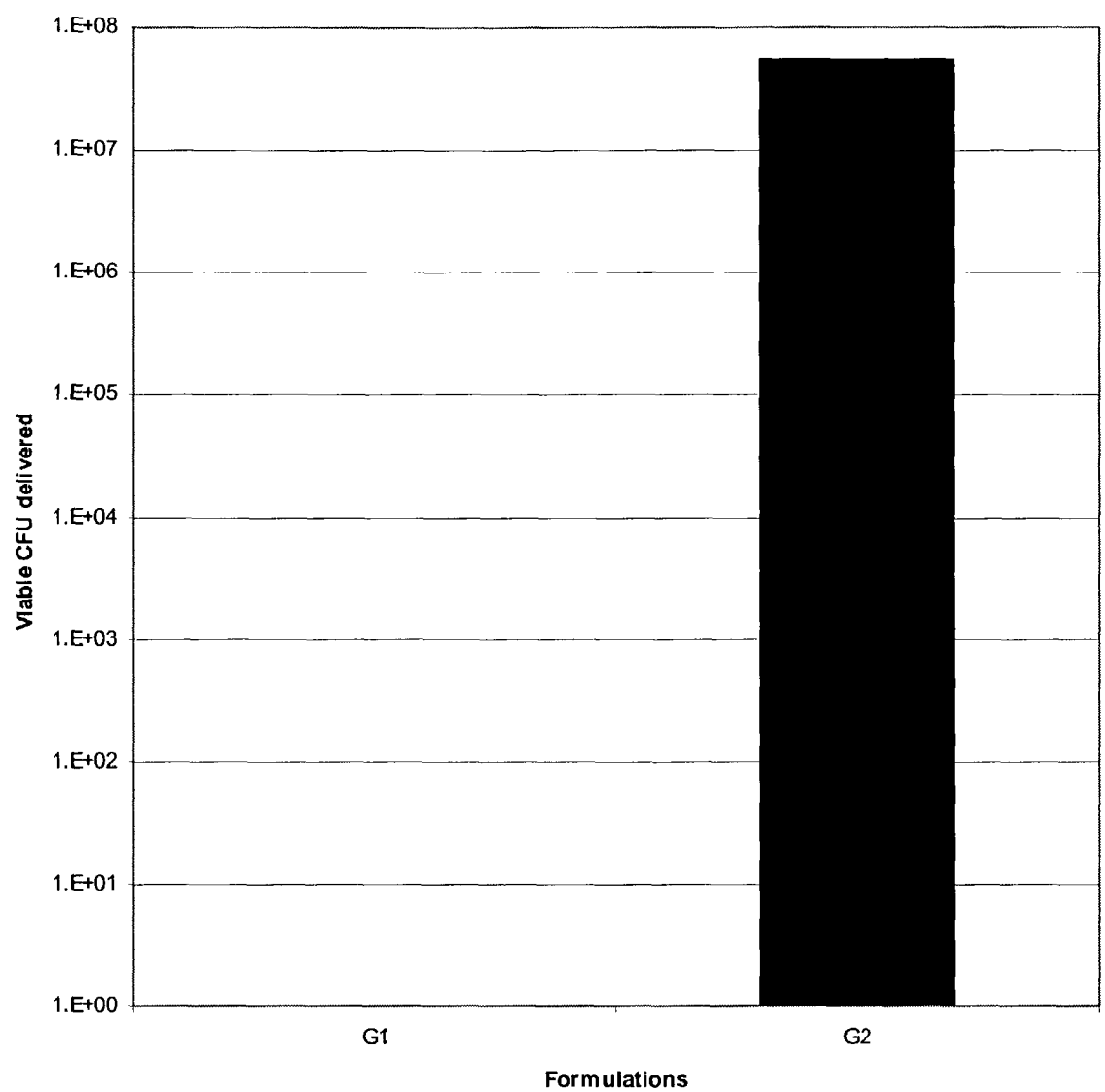
FIG. 9 shows the effects of a hydrophilic matrix on the controlled release of viable beneficial microorganisms into the small intestine from capsules.

This example, as depicted in FIG. 9, demonstrates that the combination of a hydrophilic agents, an electrolyte, and a release-modifying excipient are capable of controlling the release of the BC from a capsule. Dosage form flexibility, such as formulation for a tablet or capsule, provides substantial adaptability during manufacture.

TABLE 9

| Dosage Formulas (mg) | G1 (CTRL) | G2 |
| --- | --- | --- |
| Lactic acid bacteria pre-blend | 150 | 150 |
| Pectin | 0 | 75 |
| HPMC | 0 | 110 |
| NaHCO$_3$ | 0 | 110 |
| Guar | 0 | 200 |
| Stearic acid | 10 | 10 |
| Silica | 10 | 10 |
| TOTAL WEIGHT | 170 | 665 |

Example 10

Monolithic tablets of approximately 684 mg and 342 mg containing a hydrophilic agent, an electrolytic agent, a release-modifying excipient, a filler, and a BC was prepared as shown in Table 10. The hydrophilic polymer employed is HPMC, the electrolytic agent is NaHCO₃, the release-modifying excipient employed is pectin, the filler employed is the MCC, and the lactic acid bacteria pre-blend of lyophilized powder and starch is the BC. Stearic acid is included as a flow agent and silica is employed as flow agent and desiccant.

Figure 10:
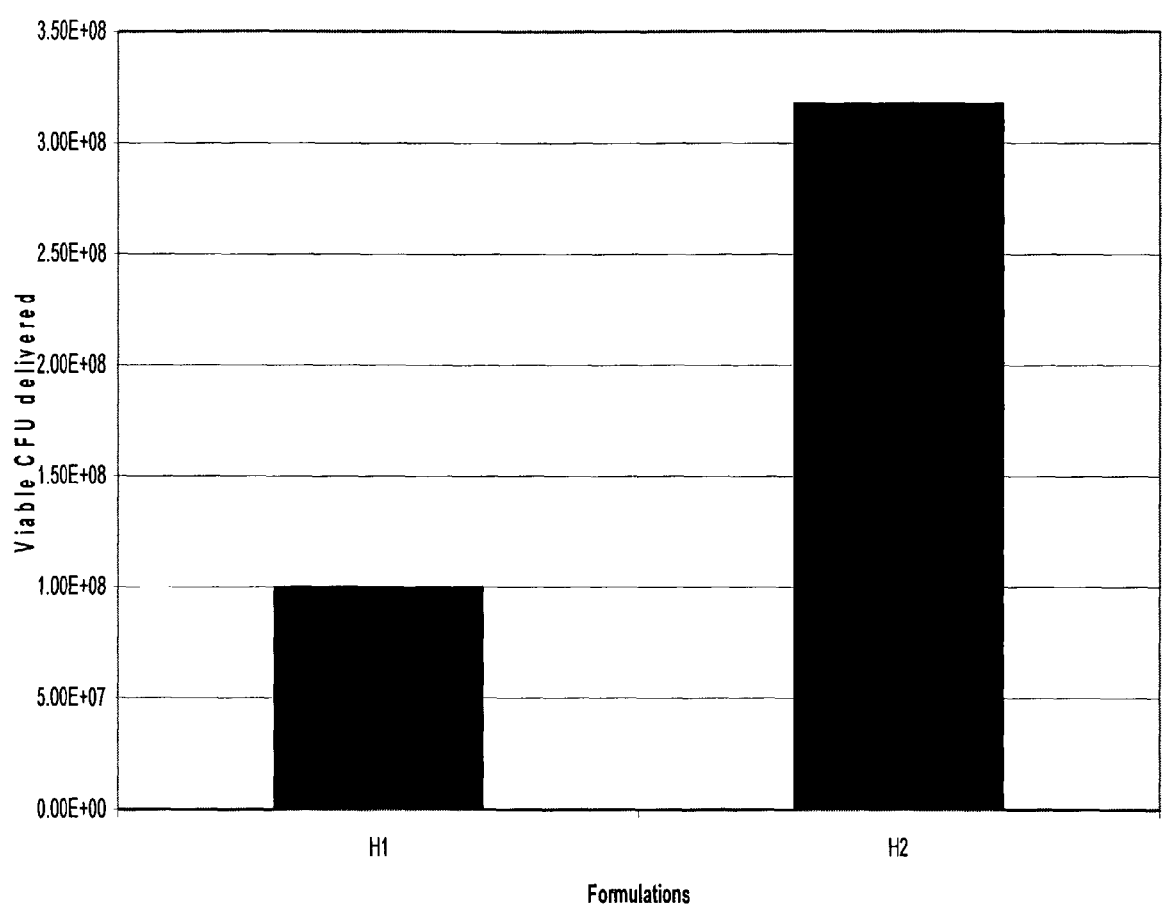
FIG. 10 shows the capacity for geometric scalability and tablet size and shape variation in the present invention and the effect of such changes on the controlled release of viable beneficial microorganisms into the small intestine from monolithic tablets.

This example, as depicted in FIG. 10, demonstrates that the combination of a hydrophilic agent, and electrolyte, and a release-modifying excipient are capable of geometric scalability, tablet shape, size and volume variation while controlling the release of the BC from the matrix. This flexibility is especially useful in manufacture when differing formulation volumes are required when altering tablet shapes and sizes.

TABLE 10

| Dosage Formulas (mg) | H1 | H2 |
|---|---|---|
| Lactic acid bacteria pre-blend | 75 | 150 |
| HPMC | 50 | 100 |
| Pectin | 50 | 100 |
| NaHCO₃ | 50 | 100 |
| MCC | 100 | 200 |
| Stearic acid | 8 | 16 |
| Silica | 8 | 16 |
| Turmeric | 1 | 2 |
| TOTAL WEIGHT | 342 | 684 |

Example 11

Monolithic tablets of approximately 684 mg containing a hydrophilic agent, an electrolytic agent, a release-modifying excipient, a filler, and a BC was prepared as shown in Table 11. The hydrophilic polymer employed is HPMC, the electrolytic agent is NaHCO₃, the release-modifying excipient employed is pectin, the filler employed is the MCC, and the lactic acid bacteria pre-blend of lyophilized powder and starch is the BC. Stearic acid is included as a flow agent and, Silica is employed as flow agent and desiccant. Tumeric is included as a colorant.

Figure 11:
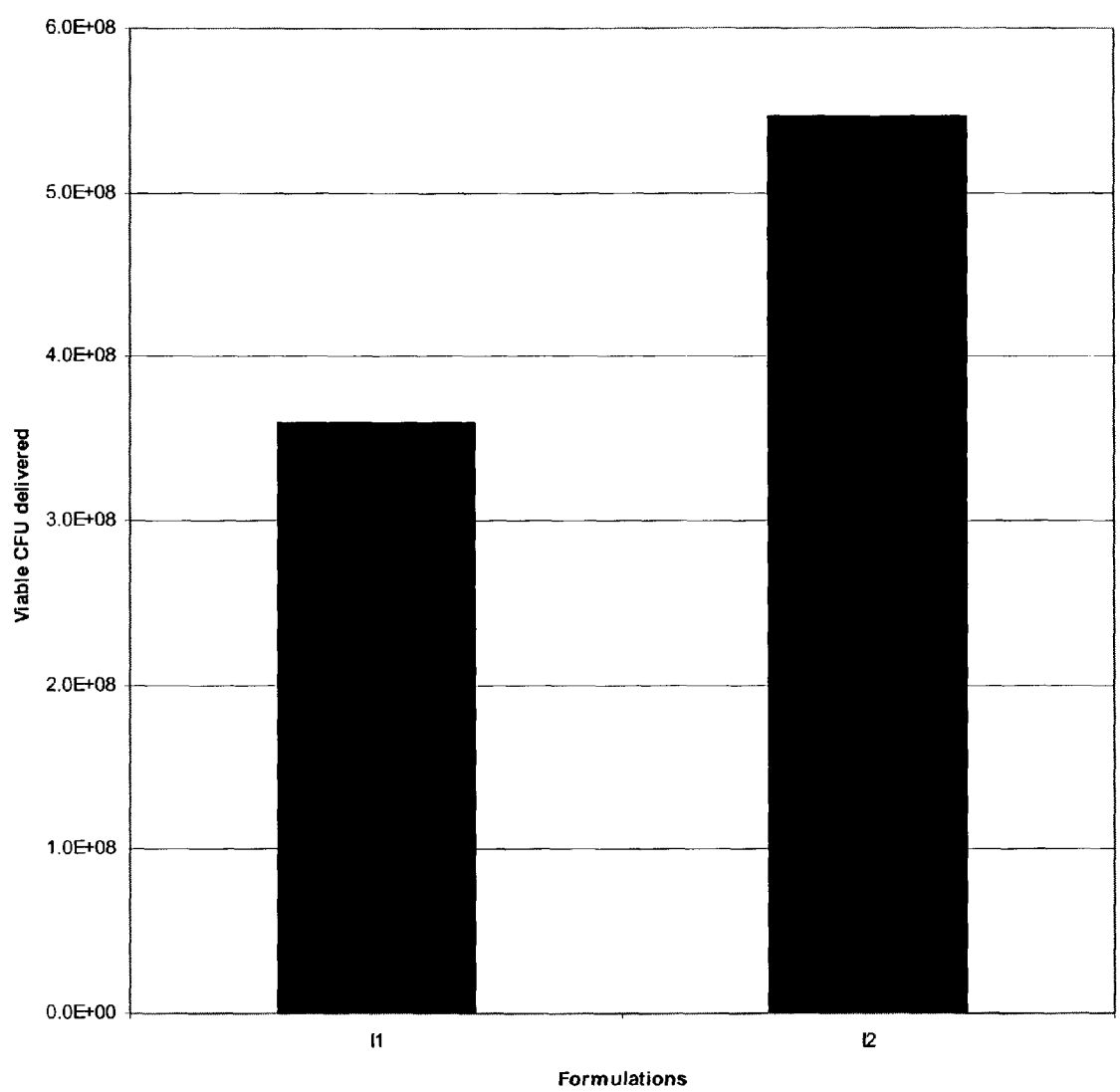
FIG. 11 shows the drying the excipients prior to tableting and the effect of such changes on the controlled release of viable beneficial microorganisms into the small intestine from monolithic tablets.

This example, as depicted in FIG. 11, demonstrates the application of drying an identical formulation of excipients of a pre-blend before tableting (I2) vs. a non-dried pre-blend (I1). The beneficial effects of drying are evidenced by the increase in viable lactic acid bacteria CFU present in the dried pre-blend.

TABLE 11

| Dosage Formulas (mg) | H1 | H2 |
|---|---|---|
| Lactic acid bacteria pre-blend | 150 | 150 |
| HPMC | 100 | 100 |
| Pectin | 100 | 100 |
| NAH(CO₃)₂ | 100 | 100 |
| MCC | 200 | 200 |
| Stearic acid | 8 | 8 |
| Silica | 8 | 8 |
| Turmeric | 2 | 2 |
| TOTAL WEIGHT | 684 | 684 |

Example 12

A monolithic tablet of approximately 532 mg containing a hydrophilic agent, an electrolytic agent, a release-modifying excipient, a filler, and a BC was prepared as shown in Table 12. The hydrophilic agent employed is HPMC of viscosity 4000 mPa or 15000 mPa, the electrolytic agent is NaHCO₃, the release-modifying excipient employed is pectin, the filler employed is MCC and the *bifidobacterium* pre-blend of lyophilized powder and starch is the BC. Stearic acid is included as a flow agent and silica is employed as flow agent and desiccant. Tumeric is included as a colorant.

Figure 12:
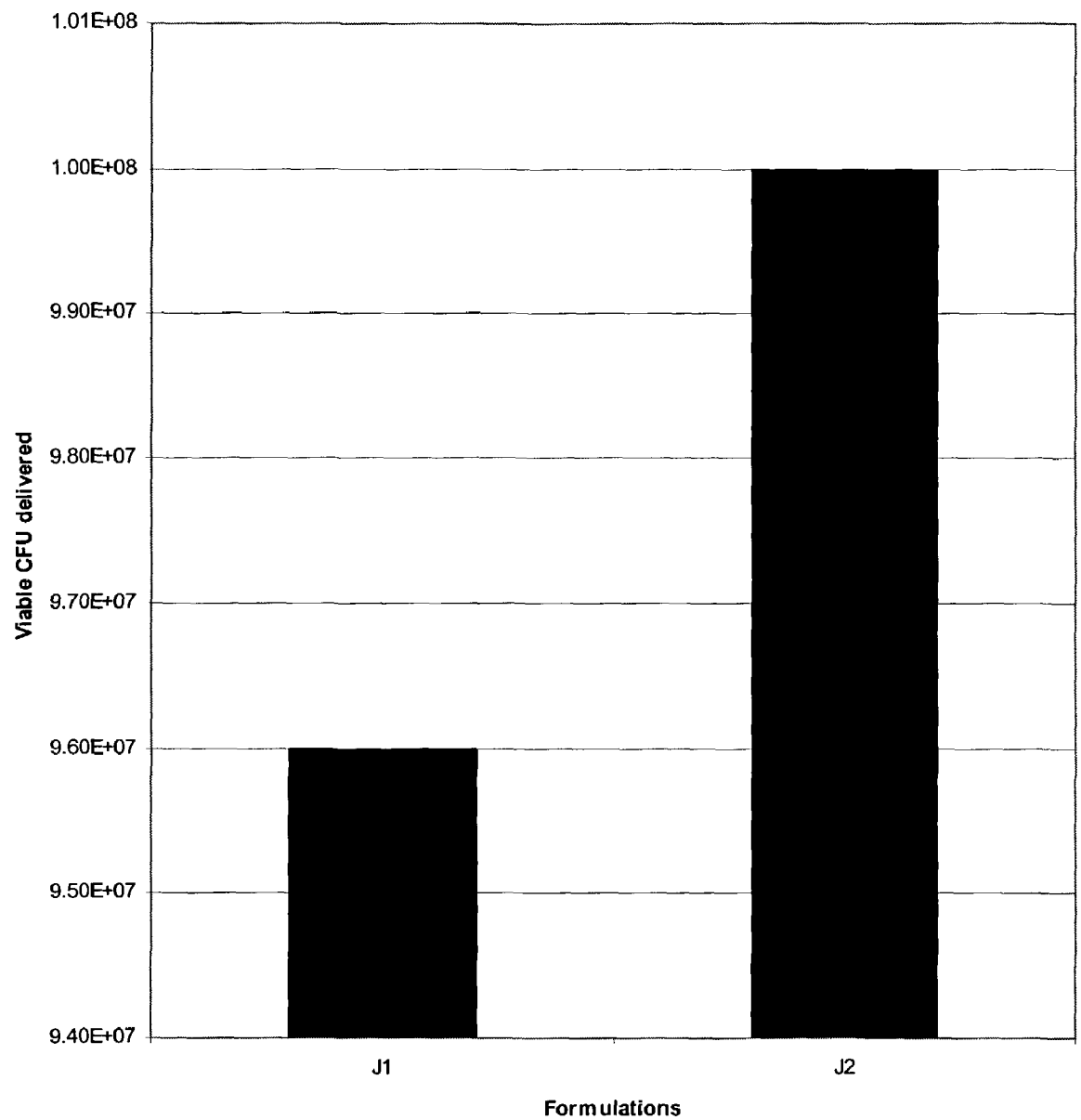
FIG. 12 shows the effects of a hydrophilic matrix employing hydrophilic polymers of differing viscosities on the controlled release of viable beneficial microorganisms into the small intestine from capsules.

As depicted in FIG. 12, the results of this example demonstrate the capacity for differential controlled release of viable BCs by employing hydrophilic agents of differing viscosities.

TABLE 12

| Dosage Formulas (mg) | H1 | H2 |
|---|---|---|
| Lactic acid bacteria pre-blend | 75 | 75 |
| HPMC, 4000 mPa | 50 | 0 |
| HPMC, 15000 mPa | 0 | 50 |
| Pectin | 50 | 50 |
| NaHCO₃ | 50 | 50 |
| MCC | 100 | 100 |
| Stearic acid | 8 | 8 |
| Silica | 8 | 8 |
| Turmeric | 1 | 1 |
| TOTAL WEIGHT | 342 | 342 |

Example 13

A monolithic tablet of approximately 343 mg containing a hydrophilic agent, an electrolytic agent, a release-modifying excipient, a filler, and a BC was prepared as shown in Table 13. The hydrophilic agent employed is HPMC, the electrolytic agent is NaHCO₃, the release-modifying excipient employed is pectin, the filler employed is MCC and the lactic acid pre-blend of lyophilized powder and starch is the BC. Stearic acid is included as a flow agent and, Silica is employed as flow agent and desiccant. Tumeric is included as a colorant.

Figure 13:
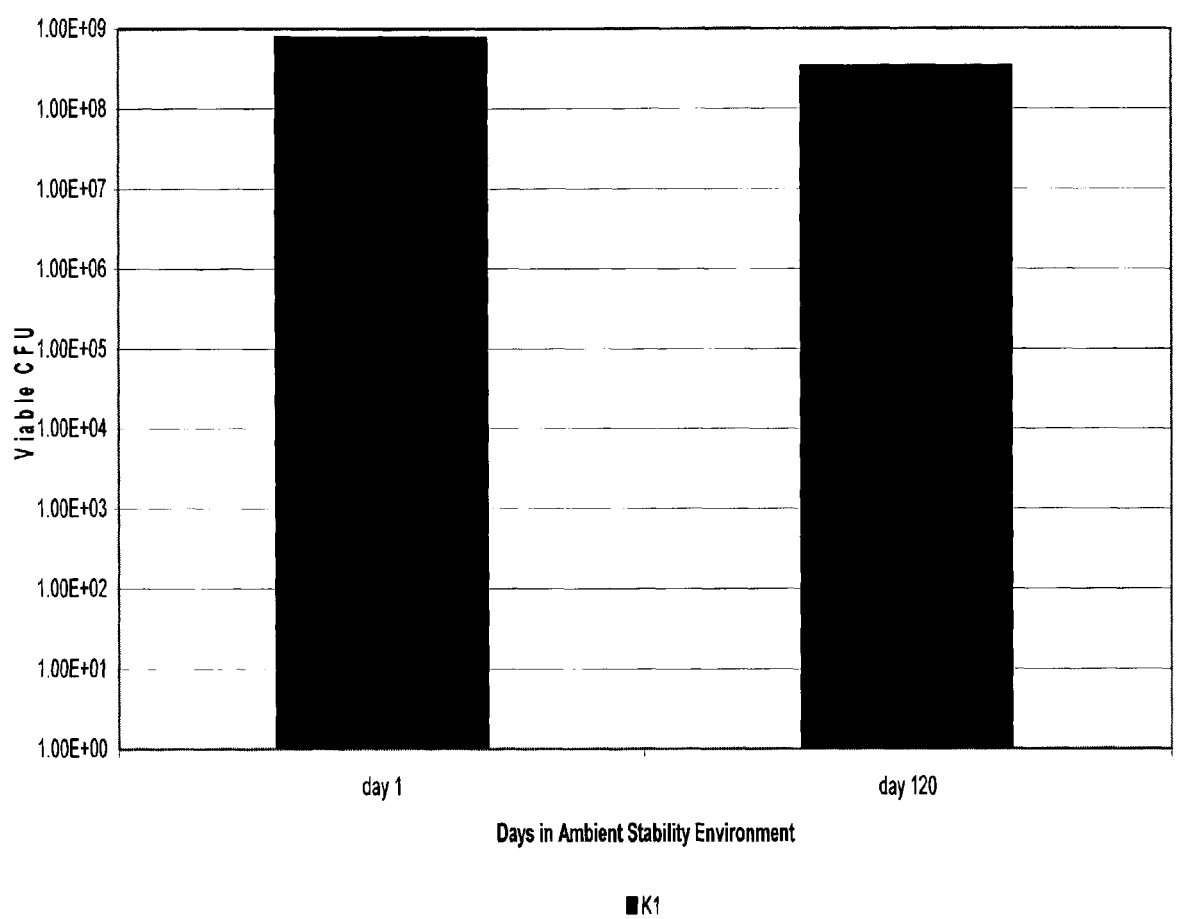
FIG. 13 shows the effects of physiologically acceptable electrolytic substances on the stability of the dosage form.

As depicted in FIG. 13, the results of this example demonstrate the capacity for increased stability over time when stored in an ambient environment, (25 degrees C., 60% Relative Humidity), evidenced by a relatively constant amount of viable lactic acid bacteria CFU.

TABLE 13

| Dosage Formulas (mg) | K1 |
|---|---|
| Lactic acid bacteria pre-blend | 75 |
| HPMC | 50 |
| Pectin | 50 |
| NAHCO₃ | 50 |
| MCC | 100 |
| Stearic acid | 8 |
| Silica | 8 |
| Turmeric | 2 |
| TOTAL WEIGHT | 343 |

The discussion above is descriptive, illustrative and exemplary and is not to be taken as limiting the scope defined by any appended claims.

We claim:

1. A controlled release formulation for oral delivery to an intestinal system, the formulation comprising:
   about 5% to 40% by total weight of at least one of a hydrophilic agent selected from the group consisting of hydroxypropyl methylcellulose and polyethylene oxide;
   about 5% to 40% by total weight of a release modifying agent comprising pectin;

about 1% to 40% by total weight of at least one of an electrolytic agent selected from the group consisting of sodium carbonate, sodium bicarbonate, sodium phosphate, and calcium carbonate; and a probiotic;

wherein said formulation is a monolithic tablet without an enteric coating.

2. The formulation of claim 1 wherein the probiotic is a lactic acid bacteria.

3. The formulation of claim 1 wherein the hydrophilic agent is hydroxypropyl methylcellulose.

4. The formulation of claim 1 wherein the hydrophilic agent is polyethylene oxide.

5. The formulation of claim 1 wherein the electrolytic agent is sodium carbonate.

6. The formulation of claim 1 wherein the electrolytic agent is sodium bicarbonate.

7. The formulation of claim 1 wherein the electrolytic agent is sodium phosphate.

8. The formulation of claim 1 wherein the electrolytic agent is calcium carbonate.

* * * * *